(12) United States Patent
Kokkinis

(10) Patent No.: US 12,208,067 B2
(45) Date of Patent: Jan. 28, 2025

(54) LIQUID DISPERSIBLE CURCUMINOID COMPOSITIONS AND METHODS OF IMPROVING COGNITIVE FUNCTION

(71) Applicant: PHARMAKO BIOTECHNOLOGIES PTY LTD, Frenchs Forest (AU)

(72) Inventor: George Kokkinis, Frenchs Forrest (AU)

(73) Assignee: Pharmako Biotechnologies Pty Ltd., New South Wales (AU)

( * ) Notice: Subject to any disclaimer, the term of this patent is extended or adjusted under 35 U.S.C. 154(b) by 0 days.

(21) Appl. No.: 18/012,382

(22) PCT Filed: Jun. 27, 2021

(86) PCT No.: PCT/AU2021/050679
§ 371 (c)(1),
(2) Date: Dec. 22, 2022

(87) PCT Pub. No.: WO2021/258163
PCT Pub. Date: Dec. 30, 2021

(65) Prior Publication Data
US 2023/0225992 A1    Jul. 20, 2023

(30) Foreign Application Priority Data

Jun. 26, 2020 (AU) ............... 2020902157
Apr. 5, 2021 (AU) ............... 2021900990

(51) Int. Cl.
*A61K 31/12* (2006.01)
*A61K 33/26* (2006.01)
*A61P 25/28* (2006.01)

(52) U.S. Cl.
CPC .............. *A61K 31/12* (2013.01); *A61K 33/26* (2013.01); *A61P 25/28* (2018.01)

(58) Field of Classification Search
CPC .... A61K 31/12; A61K 33/26; A61K 69/9066; A61K 9/1075; A61K 9/10; A61K 2300/00; A61K 47/02; A61K 47/14; A61K 47/22; A61K 47/24; A61K 47/44; A61P 25/28

See application file for complete search history.

(56) References Cited

FOREIGN PATENT DOCUMENTS

| WO | 2007103435 A2 | 9/2007 |
| WO | 2013111066 A2 | 8/2013 |
| WO | 2018187849 A1 | 10/2018 |

OTHER PUBLICATIONS

Cox, Investigation of the effects of solid lipid curcumin on cognition and mood in a healthy older population, Journal of Psychopharmacology, 2015, 29(5), pp. 642-651 (Year: 2015).*
Greig et al., Iron deficiency, cognition, mental health and fatigue in women of childbearing age: a systematic review, Journal of Nutritional Science, 2013, 2(14), pp. 1-14 (Year: 2013).*
International Search Report and Written Opinion for PCT/AU2021/050679 mailed Aug. 30, 2021, 10 pages.
Briskey, D. et al., "Increased bioavailability of curcumin using a novel dispersion technology system (LipiSperse®)", European Journal of Nutrition, 2019, vol. 58, pp. 2087-2097, <URL: https://doi.org/10.1007/s00394-018-1766-2>.
Pharmako Biotechnologies et al., "The world's most bioavailable curcumin in a single dose" [retrieved from internet on Apr. 22, 2021]. <URL: https://uploads-ssl.webflow.om/5f85d0c81b6f5da2719b6b03/5fbe0a681afa6e561c93437d_Hydrocurc-Sellsheet%20Final%20092820.pdf> published on Jan. 23, 2021 as per Wayback Machine.
Tiekou Lorinczova, H. et al., "Co-Administration of Iron and a Bioavailable Curcumin Supplement Increases Serum BDNF Levels in Healthy Adults", Antioxidants, Jul. 2020, vol. 9, iss. 8, p. 645 <URL: https://doi.org/10.3390/antiox9080645>.
Van Campen, C. et al., "The Effect of Curcumin on Patients with Chronic Fatigue Syndrome/Myalgic Encephalomyelitis: An Open Label Study", International Journal of Clinical Medicine, 2018, vol. 9, pp. 356-366, <URL: https://doi.org/10.4236/ijcm.2018.95031>.
Verdure Sciences®, "Intellectual Property" [viewed online on Aug. 10, 2021] <URL: https://vs-corp.com/ip/>published on Sep. 5, 2017 as per Wayback Machine http://web.archive.org/web/*/https://vs-corp.com/ip/.
Sara, et al, "Iron administration prevents BDNF decrease and depressive-like behavior following chronic stress" Elsevier, Oct. 2014, 9 pages.

* cited by examiner

*Primary Examiner* — Savitha M Rao
*Assistant Examiner* — Andrew P Lee
(74) *Attorney, Agent, or Firm* — LOWENSTEIN SANDLER LLP

(57) ABSTRACT

Brain-derived neurotrophic factor (BDNF) is known to be related to normal neuronal function and energy homeostasis, and increased levels of serum BDNF are associated with improved cognitive function, including learning and memory. The present invention relates generally to a method of preparing compositions for increasing the serum levels of brain-derived neurotrophic factor (BDNF). In particular, the method relates to combining a curcuminoid or a derivative thereof with a dispersing agent under high shear, and administering the composition to a subject in need thereof to increase the serum levels of Brain-derived neurotrophic factor (BDNF) to improve cognitive function, wherein the composition may be co-administered with iron.

11 Claims, 3 Drawing Sheets

Figure 1

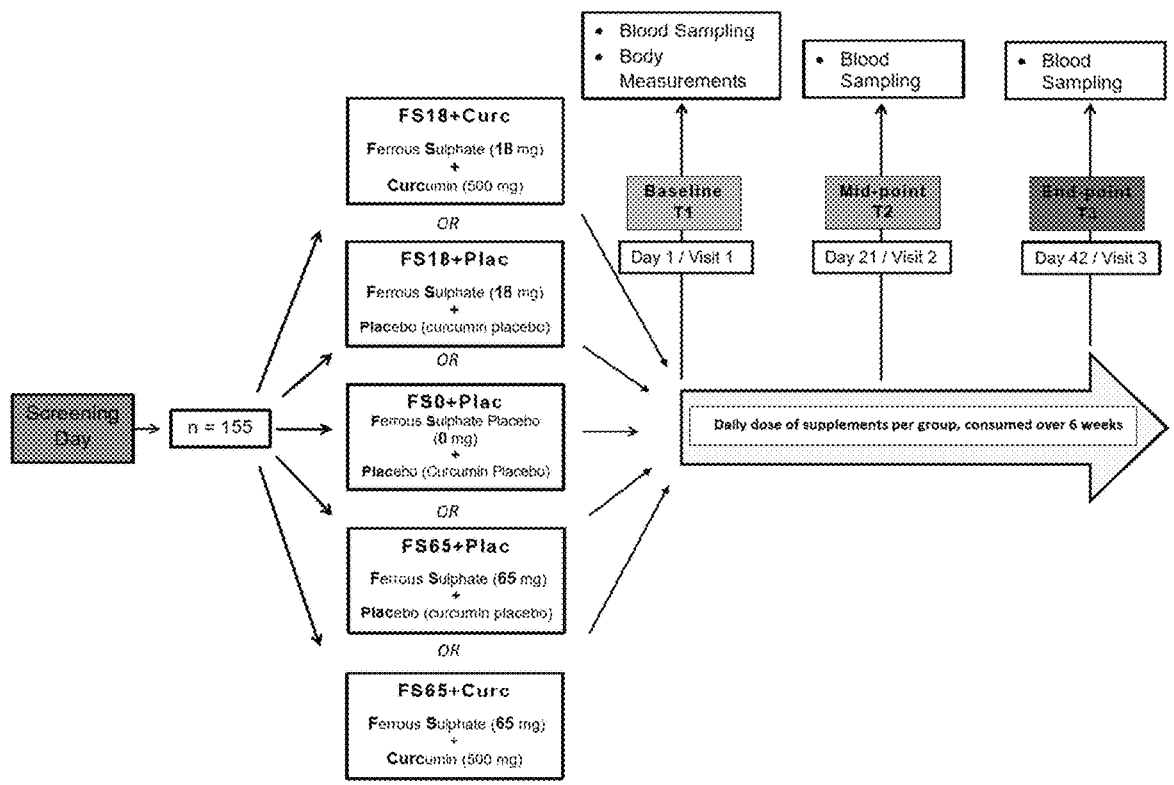

Figure 1. Study design. Participants who met the inclusion criteria during the screening day were randomly assigned to 5 different treatment groups (n = 31/group). There were three visit days over the study duration of the 6 weeks. On the first visit day (Baseline) body measurements, blood samples and questionnaires were collected from the participants. On the following visit days (Mid-point and End-point) blood samples and questionnaires were collected from the participants.

Figure 2

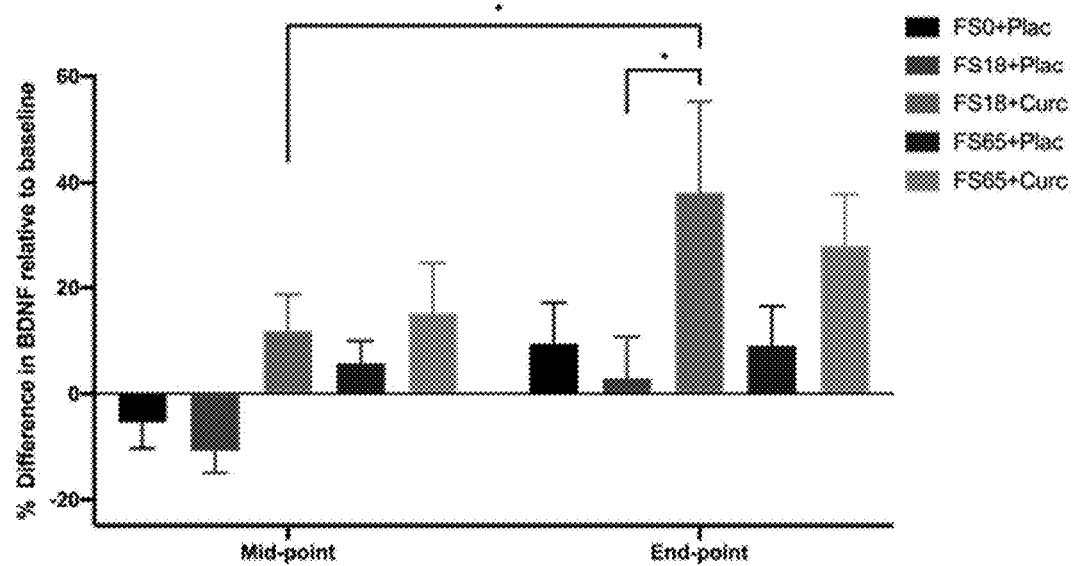

Figure 2. BDNF levels are expressed as percentage difference compared to baseline levels (mean ± SEM). FS0+Plac (Mid-point n = 29; End-point n = 28), FS18+Plac (Mid-point n = 30; End-point n = 29), FS18+Curc (Mid-point n = 31; End-point n = 31), FS65+Plac (Mid-point n = 30; End-point n = 30) and FS65+Curc (Mid-point n = 29; End-point n = 29). Samples were collected and analysed at midpoint (day 21) and endpoint (day 42). *represents significance values when comparing each condition and time points within the same condition. (* $p < 0.05$).

Figure 3

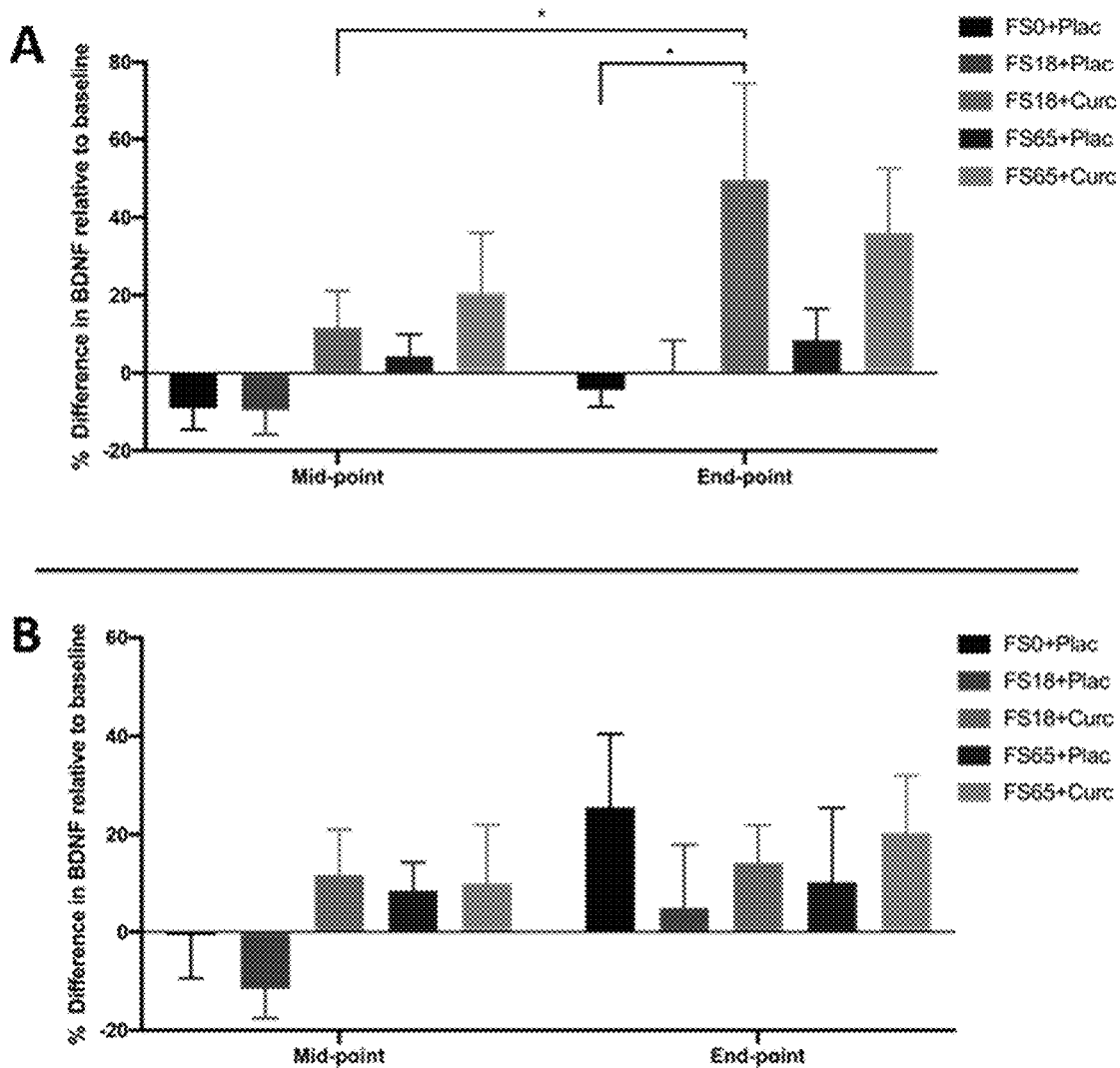

Figure 3A. Mean ± SEM, % difference in BDNF for participants with low ferritin at baseline (<50 μg/L): FS0+Plac [Mid-point n = 16; End-point: n = 15]; FS18+Plac [Mid-point n = 14; End-point n = 13]; FS18+Curc [Mid-point n = 21; End-point n = 21]; FS65+Plac [Mid-point n = 19; End-point n = 19] and FS65+Curc [Mid-point n = 14; End-point n = 14]. Samples were collected and analysed at midpoint (day 21) and endpoint (day 42). Figure 3B. Mean ± SEM, % difference in BDNF for participants with normal ferritin (≥50 μg/L): FS0+Plac [Mid and End-point n = 15]; FS18+Plac [Mid and End-point n = 16]; FS18+Curc [Mid and End-point n = 10]; FS65+Plac [Mid and End-point n = 11] and FS65+Curc [Mid and End-point n = 15]. *represents significance values when comparing each condition and time points within the same condition. (* p < 0.05).

LIQUID DISPERSIBLE CURCUMINOID COMPOSITIONS AND METHODS OF IMPROVING COGNITIVE FUNCTION

CROSS REFERENCE TO RELATED APPLICATION(S)

The present application is a national stage entry under 35 U.S.C. § 371 of International Patent Application No. PCT/AU2021/050679 filed on Jun. 27, 2021, which claims priority to Australian Patent Nos. 2020902157 filed on Jun. 26, 2020 and 2021900990 filed on Apr. 5, 2021, the entirety of which is incorporated herein by reference.

TECHNICAL FIELD

The present invention relates generally to a method of preparing compositions for increasing the serum levels of brain-derived neurotrophic factor (BDNF). In particular, the method relates to combining a curcuminoid or a derivative thereof with a dispersing agent under high shear, and administering the composition to a subject in need thereof to increase the serum levels of Brain-derived neurotrophic factor (BDNF) to improve cognitive function, wherein the composition may be co-administered with iron.

BACKGROUND ART

Any discussion of the prior art throughout the specification should in no way be considered as an admission that such prior art is widely known or forms part of common general knowledge in the field.

The use of hydrophobic compounds with health benefits as orally administrable drugs, nutraceuticals or supplements can be limited due to their poor absorption by the gastrointestinal (GI) tract. Consequently, in order to achieve any therapeutic benefit from such compounds, the dosing levels must be substantially increased.

Alternatively, methods may be employed to increase the bioavailability of the hydrophobic compound to improve or produce therapeutic benefits that may not be achievable without sufficient absorption by the GI tract.

For compounds such as the curcuminoids, the improvement in bioavailability would be beneficial for the treatment of prevention of diseases or disorders associated with cognitive function and/or energy homeostasis. This is because, despite the lipophilic curcuminoids being hypothesised to be able to cross the blood brain barrier and possible having desirable properties that may be useful for the treatment of neurological disorders, the fact that they are metabolised so quickly after ingestion means the curcuminoids are unlikely to even access the brain.

Brain-derived neurotrophic factor (BDNF) is known to be related to normal neuronal function and energy homeostasis, and increased levels of serum BDNF are associated with improved cognitive function, including learning and memory. As BDNF is known the cross the blood-brain barrier, mechanisms of regulating the serum BDNF levels are also of consequence when considering ways to optimise the beneficial effects of serum BDNF. One such regulatory pathway is thought to be regulated by interactions between iron and BDNF, wherein low brain iron levels may result in a down-regulation of BDNF.

SUMMARY OF THE INVENTION

The present inventors have found that when a curcuminoid is combined with small amounts of dispersing agents under high shear forces, the treated composition is more easily dispersed in water, and the enhanced dispersibility is accompanied by an increase in bioavailability. As a direct result of this improved bioavailability, the present inventors have surprisingly found that a dispersible curcuminoid composition can increase the serum levels of brain-derived neurotrophic factor (BDNF). This effect is further enhanced when the dispersible curcuminoid composition is combined with, or co-administered with, an iron supplement.

Accordingly, in a first aspect of the invention, there is provided a method of increasing the serum levels of brain-derived neurotrophic factor (BDNF) in said subject in need thereof, comprising the step of administering to said subject a liquid dispersible curcuminoid composition comprising curcuminoid and a dispersing agent, wherein the liquid dispersible curcuminoid composition is prepared by combining the curcuminoid with the dispersing agent whilst applying a shear force.

In an aspect of the invention, there is provided a method of improving cognitive function in a subject by increasing the serum levels of brain-derived neurotrophic factor (BDNF) in said subject, comprising the step of administering to said subject a liquid dispersible curcuminoid composition comprising curcuminoid and a dispersing agent, wherein the liquid dispersible curcuminoid composition is prepared by combining the curcuminoid with the dispersing agent whilst applying a shear force.

In another aspect of the invention, there is provided a method of improving cognitive function in a subject by increasing the serum levels of brain-derived neurotrophic factor (BDNF) in said subject, comprising the step of administering to said subject a liquid dispersible curcuminoid composition comprising curcuminoid and a dispersing agent, in combination with a source of iron, wherein the liquid dispersible curcuminoid composition is prepared by combining the curcuminoid with the dispersing agent whilst applying a shear force.

In a further aspect of the invention, there is provided a method of increasing the serum levels of brain-derived neurotrophic factor (BDNF) in a subject in need thereof, comprising the step of administering to said subject a liquid dispersible curcuminoid composition comprising curcuminoid and a dispersing agent, in combination with a source of iron, wherein the liquid dispersible curcuminoid composition is prepared by combining the curcuminoid with the dispersing agent whilst applying a shear force.

In another aspect of the invention, there is provided a method of decreasing fatigue in a subject by increasing the serum levels of brain-derived neurotrophic factor (BDNF) in said subject, comprising the step of administering to said subject a liquid dispersible curcuminoid composition comprising curcuminoid and a dispersing agent, wherein the liquid dispersible curcuminoid composition is prepared by combining the curcuminoid with the dispersing agent whilst applying a shear force.

In another aspect of the invention, there is provided a method of decreasing fatigue in a subject by increasing the serum levels of brain-derived neurotrophic factor (BDNF) in said subject, comprising the step of administering to said subject a liquid dispersible curcuminoid composition comprising curcuminoid and a dispersing agent, in combination with a source of iron, wherein the liquid dispersible curcuminoid composition is prepared by combining the curcuminoid with the dispersing agent whilst applying a shear force.

In embodiments of the invention wherein the liquid dispersible curcuminoid composition is administered in combination with a source of iron, the source of iron and the liquid dispersible curcuminoid composition may be co-administered as two separate compositions, either simultaneously or sequentially, or may be co-administered as a single composition. In embodiments where the liquid dispersible curcuminoid composition and source of iron are administered as a single composition, the single composition may be produced by combining the source of iron with the liquid dispersible curcuminoid composition after the curcuminoid and dispersing agent are combined by the application of a sheer force, or, alternatively, the source of iron may be combined with the curcuminoid and dispersing agent prior to the application of the sheer force.

BRIEF DESCRIPTION OF THE DRAWINGS

FIG. 1 illustrates a flow chart describing the study design of the Examples.
FIG. 2 is a graph evaluating the BDNF levels at mid point and end point of the study.
FIG. 3 illustrates the difference in BDNF levels relative to baseline of participants with low ferritin (A) and normal ferritin (B).

DETAILED DESCRIPTION OF INVENTION

By curcuminoid is meant a linear diarylheptanoid, such as curcumin or derivatives thereof. The curcuminoid of the present invention may be obtained from commercially available sources and/or prepared, isolated or derived for source material. The curcuminoid may be a synthetic compound, a natural compound or a semi-synthetic compound. For example, the compound may be chemically synthesised, isolated from a plant source, or may be in the form of an extract from an a or plant source, or combinations thereof.

Curcuminoid extracts from plant sources may be prepared by methods known to those skilled in the art and may include processes such as water extractions, chromatographic extractions, solvent extractions, lipid-phase and solid phase extractions, precipitations steps, drying steps, and clarification and purification steps.

The most common curcuminoid is curcumin, which is a natural polyphenol derived most abundantly from turmeric (*Curcuma longa*). Curcumin has pleiotropic molecular effects and has been used in traditional medicine to treat various disorders, and in particular, inflammation. In one or more embodiments of the present invention, the curcuminoid is selected from the group consisting of curcumin, demethoxycurcumin and bisdemethoxycurcumin. In embodiments of the present invention, the curcuminoid is in the form of an extract from a plant source, wherein the plant source is selected from the group consisting of turmeric, Devil's Claw, White Willow, ginger, grape seed extract, Giant knotweed and green tea.

The source of iron may be any compound, composition or supplement that, when administered to a subject, results in an increase in the serum iron, ferritin and/or transferrin concentration of said subject. It would be understood that ferritin is a protein that contain iron and is the primary form of iron stored inside cells, so an increase in serum ferritin concentrations can generically be considered an increase in iron in the body of the subject. The source of iron may be in the form any iron preparation, including any compound, composition or supplement that comprises heme irons, ferric carboxymaltose, iron polymaltose, ferrous sulfate, iron sucrose, ferrous gluconate, ferrous fumarate, and/or non-heme irons (plant irons), elemental iron, and combinations thereof. In preferred embodiments of the invention, the source of iron is any compound, composition or supplement that comprises at least 40% (w/w) at least 50% (w/w), at least 60% (w/w), at least 70% (w/w), at least 80% (w/w) or at least 90% (w/w) ferrous sulfate and/or ferrous fumarate, and/or ferrous gluconate, or combinations thereof.

The source of iron may also be characterised in the context of the percentage by weight of elemental iron in said source, on the understanding that, for example, ferrous fumarate comprises approximately 33% (w/w) elemental iron, ferrous sulphate comprises approximately 20% (w/w) elemental iron and ferrous gluconate comprises approximately 12% (w/w) elemental iron. Accordingly, in embodiments of the invention where the source of iron is defined in the context of its elemental iron content, the source of iron is any compound, composition or supplement that comprises at least 5% (w/w), at least 10% (w/w), at least 15% (w/w), at least 20% (w/w) or at least 25% (w/w), or at least 30% (w/w) elemental iron.

Generally, the dispersing agent is a compound or composition which, when present on the surface of particles of the solid substance, increases the wettability of the curcuminoid, thereby improving dispersion of the curcuminoid in a liquid. A liquid-dispersible curcuminoid composition will separate relatively uniformly in a liquid, without significant observable aggregation and/or agglomeration.

Whether the composition is liquid dispersible (or has improved dispersion properties) may be determined by the average particle size achieved when the liquid dispersible curcuminoid composition produced by the methods of the invention is mixed with water. In one or more embodiments of the present invention, the liquid dispersible composition produces a population of particles when mixed with water, wherein greater than 50% of the population of particles are between 1 and 100 μm in diameter. Preferably, the particles are between 1 and 50 μm in diameter.

The method of the present invention improves the bioavailability of the curcuminoid in the liquid dispersible curcuminoid composition. In general, the bioavailability of a compound is an indicator of the degree and rate a compound enters the circulatory system when introduced through ingestion, inhalation, injection, or skin contact. In embodiments of the invention, the bioavailability of the hydrophobic compound in the solid substance is increased after combining said curcuminoid with the dispersing agent whilst applying a shear force. Preferably, the bioavailability of the curcuminoid in the liquid dispersible curcuminoid composition is increased by at least about 20%, 30%, 50%, 60%, 70%, 80%, 90%, 100%, 120%, 150% or 200% and above when compared to the bioavailability of the same curcuminoid that has not been combined with the dispersing agent whilst applying a shear force.

In certain embodiments of the present invention, the dispersing agent comprises an amphiphilic molecule, comprising a hydrophobic portion and a hydrophilic portion, such as a surfactant. The surfactant may be any compound or composition suitable for producing mixtures of substances that would not ordinarily mix by, for example, lowering the surface tension of between a liquid and solid. In general, a surfactant consists of a hydrophilic head and a hydrophobic tail. The surfactant may be an ionic (cationic or anionic) surfactant, a zwitterionic surfactant, a phospholipid surfactant or a non-ionic surfactant, or combinations thereof.

The dispersing agent may comprise more than one surfactant, and the surfactants may be the same type or a different type. For example, the dispersing agent may comprise two phospholipid surfactants and a non-ionic surfactant. In another example, the dispersing agent may comprise two non-ionic surfactants. In a further example, the dispersing agent may comprise a phospholipid surfactant, an anionic surfactant and a non-ionic surfactant. In preferred embodiments of the invention, the dispersing agent comprises an amphiphilic molecule that is a non-ionic surfactant.

The surfactant may be selected from the group consisting of hydrogenated castor oil, lecithin, macrogolglycerol hydroxystearate, oat oil, polar lipids, phosphatidylcholine, poloxamers, castor oil ethoxylate (i.e. ETOCAS; polyoxyl castor oil), polysorbate 20, polysorbate 60, polysorbate 80, polyglycerol polyricinoleate, D-alpha-tocopherol polyethylene glycol 1000 succinate (TPGS), glyceryl monooleate and polyglycerol esters of fatty acids. In preferred embodiments of the invention, the dispersing agent comprises a non-ionic surfactant and/or a phospholipid surfactant. The dispersing agent may comprise one or more surfactants, wherein the total amount of surfactant in the dispersing agent is 5% (w/w)-99% (w/w). Preferably, the total amount of surfactant in the dispersing agent is 10% (w/w)-90% (w/w). In other embodiments, the total amount of surfactant in the dispersing agent is 50% (w/w)-75% (w/w), or 10% (w/w)-25% (w/w), 50% (w/w)-99% (w/w), 20% (w/w)-75% (w/w), 5% (w/w)-15% (w/w).

For example, the dispersing agent may comprise about 0.5% (w/w)-10% (w/w) of one or more phospholipid surfactants and 60% (w/w)-99% (w/w) of one or more non-ionic surfactants, or the dispersing agent may comprise a total of at least about 2.5% (w/w)-10% (w/w) phospholipid surfactants and a total of at least 70% (w/w)-99% (w/w) of non-ionic surfactants. In other examples, the dispersing agent may only comprise one surfactant at about 50% (w/w)-70% (w/w), or dispersing agent may comprise about 0.2% (w/w)-10% (w/w) of one surfactant such as lecithin and 60% (w/w)-99% (w/w) of a different surfactant, such as hydrogenated castor oil, castor oil ethoxylate, or a derivative or precursor thereof.

In other examples, the dispersing agent may comprise 60% (w/w)-99% (w/w) hydrogenated castor oil and/or castor oil ethoxylate, 0.2% (w/w)-2.5% (w/w) lecithin and/or oat oil, and/or 0.5% (w/w)-5% (w/w) glyceryl monooleate, or the dispersing agent may comprise 5% (w/w)-50% (w/w) phospholipid surfactant, and 0.5% (w/w)-5% (w/w) of a different surfactant. In a further example, the dispersing agent comprises two or more surfactants selected from the group consisting of hydrogenated castor oil, castor oil ethoxylate, lecithin, macrogolglycerol hydroxystearate, oat oil, polar lipids, phosphatidylcholine, poloxamers, polyoxyl 35 castor oil, polyoxyl 40 castor oil, polysorbate 20, polysorbate 60, polysorbate 80, polyglycerol polyricinoleate, D-alpha-tocopherol polyethylene glycol 1000 succinate (TPGS), glyceryl monooleate and polyglycerol esters of fatty acids, wherein each of the surfactants are present at a concentration of 0.5% (w/w)-70% (w/w). In preferred embodiments of the invention, the dispersing agent comprises an about 50% (w/w) to about 90% (w/w) non-ionic surfactant in the form of hydrogenated castor oil and/or castor oil ethoxylate.

In one or more embodiments of the invention, the dispersing agent further comprises a carrier oil selected from the group consisting of medium chain triglycerides, long chain triglycerides, caprylic and/or capric triglycerides, coconut oil, corn oil, cottonseed oil, olive oil, sesame oil, soybean oil, peanut oil, castor oil and oleic acid. The dispersing agent may comprise one or more carrier oils, wherein the total amount of carrier oil in the dispersing agent is 1% (w/w)-50% (w/w). Preferably, the total amount of carrier oil in the dispersing agent is 5% (w/w)-30% (w/w). More preferably, the total amount of carrier oil in the dispersing agent is 10% (w/w)-25% (w/w). In other preferred embodiments, the dispersing agent comprises 10% (w/w)-25% (w/w) carrier oil in the form of medium chain triglycerides, long chain triglycerides, and/or caprylic and/or capric triglycerides, or combinations thereof. In other preferred embodiments, the dispersing agent comprises 10% (w/w)-25% (w/w) carrier oil in the form of medium chain triglycerides.

In one or more embodiments of the invention, the dispersing agent comprises two or more carriers oils selected from the group consisting of medium chain triglycerides, long chain triglycerides, caprylic and/or capric triglycerides, coconut oil, corn oil, cottonseed oil, olive oil, sesame oil, soybean oil, peanut oil, castor oil and oleic acid, wherein each of the carrier oils is present at a concentration of 0.5% (w/w)-10% (w/w), or 1.5% (w/w)-20% (w/w). In further embodiments of the invention, the dispersing agent comprises medium chain triglycerides, olive oil and/or coconut oil at a total concentration of 15% (w/w)-30% (w/w).

In other embodiments of the invention, the dispersing agent further comprises a solvent selected from the group consisting of citrus oil, ethanol, ethyl oleate, glycerine, glyceryl mono-oleate, limonene, polyethylene glycol 300, polyethylene glycol 400, polyethylene glycol 600 and propylene glycol. The dispersing agent may comprise one or more solvents, wherein the total amount of solvent is 1% (w/w)-30% (w/w). More preferably, the total amount of solvent in the dispersing agent is 1% (w/w)-10% (w/w). In preferred embodiments, the dispersing agent comprises 0.5%-15% (w/w) citrus oil, and/or 0.5%-25% (w/w) a poly ethylene glycol.

In one or more embodiments of the present invention, the dispersing agent comprises an amphiphilic molecule and a carrier oil. In other embodiments, the dispersing agent comprises an amphiphilic molecule and solvent. In preferred embodiments, the dispersing agent comprises an amphiphilic molecule, a solvent and a carrier oil. In preferred embodiments, the dispersing agent comprises 10% (w/w)-99% (w/w) total surfactant, 1% (w/w)-30% (w/w) total solvent and 5% (w/w)-30% (w/w) total carrier oil. In preferred embodiments, the dispersing agent comprises 50% (w/w)-75% (w/w) total surfactant, 2.5% (w/w)-15% (w/w) total solvent and 10% (w/w)-25% (w/w) total carrier oil.

In other preferred embodiments, the dispersing agent comprises 50% (w/w)-75% (w/w) total surfactant, wherein the surfactant comprises a non-ionic surfactant, 2.5% (w/w)-15% (w/w) total solvent, wherein the solvent comprises citrus oil, and 5% (w/w)-10% (w/w) total carrier oil, wherein the carrier oil comprises medium chain glycerides.

In other examples, the dispersing agent may comprise 60% (w/w)-75% (w/w) non-ionic surfactant, 0.2% (w/w)-10% (w/w) phospholipid surfactant, 2.5% (w/w)-15% (w/w) citrus oil, and 10% (w/w)-25% (w/w) total carrier oil.

The dispersing agent may further comprise a preservative, such as an anti-microbial or an anti-oxidant. In an embodiment of the present invention, the preservative is an anti-oxidant is selected from the group consisting of ascorbyl palmitate, d alpha-tocopherol, dl-alpha-tocopherol, d-alpha-Tocopheryl acetate, di-alpha-Tocopheryl acetate, d-alpha-Tocopheryl acid succinate, dl alpha-Tocopheryl acid succinate, Vitamin E and derivatives thereof, olive polyphenols and algal polyphenols. In preferred embodiments of the invention, the dispersing agent may comprise a preservative at a concentration of 0.1%-5% (w/w).

The dispersing agent and the curcuminoid may be combined at any ratio that will facilitate the production of the liquid dispersible curcuminoid. In embodiments of the present invention, the ratio of the curcuminoid and the dispersing agent is from about 100:1 to about 1:1.

In one or more embodiments of the present invention, the curcuminoid is combined with the dispersing agent in the presence of an anti-caking agent. Anti-caking agents function by the absorption of excess moisture. By definition, anti-caking agents are anhydrous compounds that are added in small amounts to dry products to prevent the particles caking together and ensure the product remains dry and free-flowing. Non-limiting examples of anticaking agents include the stearates of calcium and magnesium, silica and various silicates, talc, as well as flour and starch. In preferred embodiments of the invention, the anti-caking agent is a silica-based agent.

A shear force is created when forces are applied to a mixture in one direction, in conjunction with forces in the opposite direction, within the same parallel plane. In the methods of the present invention, the shear force is required to embed, connect or interface the dispersing agent onto the non-wettable surfaces of the particles of the solid substance.

In one or more embodiments of the present invention, shear force is created by high shear mixing of the curcuminoid with the dispersing agent. The skilled addressee would understand that high shear mixing can be achieved by numerous methods, including, but not limited to, milling (such as ball milling, pin milling, jet milling and colloidal milling, or grinding with mortar and pestle), rotor-stator mixing, blending, chopping, high-pressure homogenisation and combinations thereof.

In an embodiment of the present invention, the liquid dispersible curcuminoid composition comprises a curcuminoid and a dispersing agent, wherein the dispersing agent comprises 10% (w/w)-99% (w/w) total surfactant, a carrier oil and a solvent, and wherein the curcuminoid is combined with the dispersing agent with high shear mixing, and the ratio of said curcuminoid and dispersing agent is from about 20:1 to about 5:1.

In preferred embodiments of the invention, the liquid dispersible curcuminoid composition comprises at least 50% (w/w), at least 60% (w/w), at least 70% (w/w), at least 80% (w/w), at least 85% (w/w), at least 90% or at least 95% (w/w) total curcuminoids.

In preferred embodiments of the invention, the liquid dispersible curcuminoid composition comprises at least 50% (w/w), at least 40% (w/w), at least 30% (w/w), at least 20% (w/w), at least 15% (w/w), at least 10% or at least 5% (w/w) total dispersing agent.

In particularly preferred embodiments of the invention, the liquid dispersible curcuminoid composition comprises at least 50% (w/w) total curcuminoids and at least 40% (w/w) total dispersing agent, at least 60% (w/w) total curcuminoids and at least 30% (w/w) total dispersing agent, at least 70% (w/w) total curcuminoids and at least 20% (w/w) total dispersing agent, at least 80% (w/w) total curcuminoids and at least 10% (w/w) total dispersing agent, at least 85% (w/w) total curcuminoids and at least 10% (w/w) total dispersing agent, or at least 80% (w/w) total curcuminoids and at least 10% (w/w) total dispersing agent.

In embodiments of the invention wherein the liquid dispersible curcuminoid composition is combined with the source of iron, the liquid dispersible curcuminoid composition and the source of iron may be combined at any ratio that enhances the increase in serum BDNF levels when compared to the administration of either the liquid dispersible curcuminoid composition and the source of iron alone. In embodiments of the present invention, the ratio of the liquid dispersible curcuminoid composition and the source of iron is from about 50:1 to about 1:1. In preferred embodiments of the invention, the ratio of the liquid dispersible curcuminoid composition and the source of iron is from about 40:1 to about 2:1. In particularly preferred embodiments of the invention, the ratio of the liquid dispersible curcuminoid composition and the source of iron is from about 20:1 to about 5:1.

In various embodiments of the uses and methods of the invention, the liquid dispersible curcuminoid composition in combination with the source of iron may be defined in the context of a ratio of total curcuminoids and elemental iron, wherein the ratio of total curcuminoids and elemental iron is from about 50:1 to about 5:1. In preferred embodiments of the invention, the ratio of total curcuminoids and elemental iron is about 30:1, about 25:1, about 20:1, about 15:1, about 10:1, or about 5:1. In other preferred embodiments of the invention, the ratio of total curcuminoids and elemental iron is about 30:1 to about 5:1.

In other embodiments of the uses and methods of the invention, the liquid dispersible curcuminoid composition in combination with the source of iron may be defined in the context of the mass amounts of total curcuminoids and elemental iron, wherein the liquid dispersible curcuminoid composition comprises about 100 mg-1000 mg total curcuminoids and the sources of iron comprises 4 mg-200 mg of elemental iron, or preferably, wherein the liquid dispersible curcuminoid composition comprises about 250 mg-750 mg total curcuminoids and the sources of iron comprises 15 mg-150 mg of elemental iron.

The liquid dispersible compositions and/or sources or iron as used in the present invention may further comprise, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavouring agent.

In a further aspect of the present invention, there is provided the use of a liquid dispersible curcuminoid composition in the manufacture of a medicament for increasing the serum BDNF level in a subject in need thereof.

In a further aspect of the present invention, there is provided the use of a liquid dispersible curcuminoid composition in the manufacture of a medicament for the treatment or prevention of a disease or disorder wherein an increase in the serum levels of BDNF provides a therapeutic benefit.

In a further aspect of the present invention, there is provided the use of a liquid dispersible curcuminoid composition in the manufacture of a medicament for the treatment or prevention of a disease or disorder associated with cognitive function and/or energy homeostasis.

In a further aspect of the present invention, there is provided a method of treating a disease or disorder associated with cognitive function and/or energy homeostasis in a subject, comprising administering to said subject a therapeutically effective amount of a liquid dispersible curcuminoid composition of the present invention, wherein the curcuminoid comprises curcumin.

In a further aspect of the present invention, there is provided a method of treating a disease or disorder wherein an increase in the serum levels of BDNF provides a therapeutic benefit in a subject, comprising administering to said subject a therapeutically effective amount of a liquid dispersible curcuminoid composition of the present invention, wherein the curcuminoid comprises curcumin.

In a further aspect of the present invention, there is provided the use of a liquid dispersible curcuminoid composition and a source of iron in the manufacture of a medicament for increasing the serum BDNF level in a subject in need thereof.

In a further aspect of the present invention, there is provided the use of a liquid dispersible curcuminoid composition and a source of iron in the manufacture of a medicament for the treatment or prevention of a disease or disorder wherein an increase in the serum levels of BDNF provides a therapeutic benefit.

In a further aspect of the present invention, there is provided the use of a liquid dispersible curcuminoid composition and a source of iron in the manufacture of a medicament for the treatment or prevention of a disease or disorder associated with cognitive function and/or energy homeostasis.

In a further aspect of the present invention, there is provided a method of treating a disease or disorder associated with cognitive function and/or energy homeostasis in a subject, comprising administering to said subject a therapeutically effective amount of a liquid dispersible curcuminoid composition of the present invention, combined with, or co-administered with iron, wherein the curcuminoid comprises curcumin and the source of iron comprises ferrous sulfate and/or ferrous fumarate.

In a further aspect of the present invention, there is provided a method of treating a disease or disorder wherein an increase in the serum levels of BDNF provides a therapeutic benefit in a subject, comprising administering to said subject a therapeutically effective amount of a liquid dispersible curcuminoid composition of the present invention, combined with or co-administered with a source of iron, wherein the curcuminoid comprises curcumin and the source of iron comprises ferrous sulfate and/or ferrous fumarate.

The liquid dispersible curcuminoid compositions, sources of iron and medicaments of the present are generally for oral administration and may be in any form and further comprise suitable excipients or additives. The forms that may be employed, include, but are not limited to, tablets or filled capsules, or liquids such as suspensions, emulsions, elixirs, or capsules filled with the same, or free flowing powders. In the context of the liquid dispersible curcuminoid compositions of the present invention being "combined" with a source of iron, this is understood the mean the liquid dispersible curcuminoid compositions are co-administered with the source of iron, though the administration route can be different or the same. For example, both the liquid dispersible curcuminoid compositions and the source of iron may be orally administered either as separate doses or in a single dose, or, in another example, the liquid dispersible curcuminoid composition may be administered orally while the source of iron is administered as an injectable.

Effective doses of the compositions, sources of iron and medicaments used in the present invention may be ascertained by conventional methods, and will generally be dependent on the amount or % (w/w) of total curcuminoids in the liquid dispersible curcuminoid compositions and the amount of % (w/w) of elemental iron in the source of iron. The specific dosage level required for any particular subject will depend on a number of factors, including the severity of the condition being treated, the base-line blood iron levels of the subject, the route of administration and the weight of the subject.

1 unit dose of a liquid dispersible curcuminoid composition or medicament of the present invention, or 1 unit of a composition comprising both the liquid dispersible curcuminoid composition and the source of iron of the present invention, preferably comprises about 100 mg to about 2000 mg total curcuminoids. In another example, the unit dose includes about 50 mg to about 1000 mg, about 100 mg to about 1000 mg, about 200 mg to about 1000 mg, about 400 mg to about 500 mg, about 500 mg to about 2000 mg, about 400 mg to about 1000 mg, or about 800 mg to about 1000 mg total curcuminoids. Preferably, the unit dose includes about 100 mg, about 200 mg, about 250 mg, about 300 mg, about 400 mg, about 450 mg, about 500 mg, about 600 mg, about 700 mg, about 800 mg, about 900 mg, or about 1000 mg total curcuminoids.

1 unit dose of a source of iron or medicament of the present invention, or 1 unit of composition comprising both the liquid dispersible curcuminoid composition and the source of iron of the present invention, preferably comprises about 4 mg to about 200 mg elemental iron. In another example, the unit dose includes about 10 mg to about 200 mg, about 5 mg to about 25, mg about 15 mg to about 150 mg, about 20 mg to about 1000 mg, about 40 mg to about 75 mg, about 50 mg to about 200 mg, about 40 mg to about 100 mg, or about 8 mg to about 25 mg total curcuminoids. Preferably, the unit dose includes about 5 mg, about 10 mg, about 15 mg, about 20 mg, about 25 mg, about 40 mg, about 45 mg, about 50 mg, about 55 mg, about 60 mg, about 65 mg, about 70 mg, or about 80 mg elemental iron.

The unit dose comprising the curcuminoids and/or the elemental iron may be administered once, twice, three, four or five times daily, or may be administered every second or third day, or once every week, once every two weeks or once every four weeks. The unit dose may be administered once, or for up to 1-4 weeks, or for up to 1-12 months, or for up to 1-5 years, or until the subject's serum BDNF levels are increased to an acceptable level.

Definitions

Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to".

The term "treatment", and the like, in the context of the present specification includes the alleviation of the symptoms related to a disease or disorder. The treatment may cure the disease or disorder. Hence, in the context of this invention the word "treatment" or derivations thereof when used in relation to a therapeutic application includes all aspects of a therapy, such as the alleviation of pain associated with the disease or disorder, alleviation of the severity of the disease or disorder, improvement in one or more symptoms of the disease or disorder, improvement in the overall well-being of the subject being treated. Use of the word "treatment" or derivatives thereof will be understood to mean that the subject being "treated" may experience any one or more of the aforementioned benefits.

The term "prevention", and the like, in the context of the present specification refers to the prevention of the recurrence of all or some of the symptoms associated with a disease or disorder, as well as the prevention of the spread of the disease or disorder.

In the context of this specification the term "about" will be understood as indicating the usual tolerances that a skilled addressee would associate with the given value.

In the context of this specification, where a range is stated for a parameter it will be understood that the parameter includes all values within the stated range, inclusive of the stated endpoints of the range.

In the context of the present invention, the term "subject" refers to an animal, preferably a mammal, most preferably a human, who has experienced and/or exhibited at least one symptom associated with a referred to disease or disorder. Further, as used herein, a "subject in need thereof" may additionally be a subject who has not exhibited any symptoms of a particular disease or disorder, but who has been deemed by, for example, a physician, clinician or other medical professional, a naturopath or other practitioner to be at risk of developing said disease or disorder. For example, the subject may be deemed to be at risk of developing a particular disease or disorder (and therefore in need of prevention or preventive treatment) as a consequence of the subject's medical history, including, but not limited to, family history, pre-disposition, co-existing/contributory injuries or disorders and genetic testing.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations or any two or more of said steps or features.

The present invention is not to be limited in scope by the specific embodiments described herein, which are intended for the purpose of exemplification only. Detailed description of the invention Preferred features, embodiments and variations of the invention may be discerned from the following detailed description which provides sufficient information for those skilled in the art to perform the invention. The detailed description is not to be regarded as limiting the scope of the preceding summary of the invention in any way.

Example 1: Liquid Dispersible Curcuminoid Composition

Batch #MT20170428_03CurcuminCWD90 was prepared with 16.08 kg of *Curcuma longa* extract and 1.61 kg of a dispersing agent prepared with 70% (w/w) Etocas 35, 20% (w/w) medium chain triglycerides, 4.5% (w/w) lime oil, 1.5% (w/w) olive oil, 2.5% (w/w) glycerol mono-oleate, 0.5% (w/w) vitamin E acetate, 0.5% (w/w) lecithin and 0.5% (w/w) oat oil, and 0.18 kg of Silica colloidal anhydrous. The extract and dispersing agent were combined with high shear mixing in a rotor-stator mixer (High Shear Mixer-LHS300, SAR Labortecnic; 100-150 rpm for impeller and 1000-2000 rpm for cutting blades, with 5 min bursts for 35 min total). The silica was only added after an initial mixing step with 100 rpm impeller speed and 1000 rpm cutting blade speed.

A sample of the resulting liquid dispersible curcuminoid composition was assayed for particle size and the mean particles size was 23.05 UM. A sample was added to water to assay the dispersion of the composition and, over time, the curcumin passively dispersed in water without mixing.

Example 2: Enhanced Bioavailability of a Liquid Dispersible Curcuminoid Composition A single equivalent dose, randomised, double blinded parallel design with crossover was used to evaluate the pharmacokinetics of a commercially availability curcumin product, with or without the curcumin-LipiSperse delivery complex (liquid dispersible curcuminoid composition). 18 healthy volunteers (9 females, 9 males) were recruited to take part in this study.

The study arms were as follows: 1) Curcumin CWD 90 with LipiSperse (Pharmako Biotechnologies, New South Wales; Batch #MT20170428_03 CurcuminCWD90 from Example 1) hard shell capsule (2×440 mg) containing about 90% *Curcuma longa* extract and 10% LipiSperse (the dispersing agent) and 2) Standard curcumin capsule (4×200 mg) containing 100% *Curcuma longa* extract. *Curcuma longa* extract contains 95% curcuminoids. Both products therefore provided a total dose of 750 mg of curcuminoids (80% curcumin, 17% DMC and 3% BDMC by weight). Participants were required to complete an overnight fast (12-hours) prior to the day of testing. Curcumin pharmacokinetics were determined from blood samples taken prior to dosing (t=0), followed by intervals of 1, 1.5, 2, 2.5, 3, 3.5, 4, 4.5, 5, 5.5, 6 and 24 hours post supplementation.

Plasma samples were extracted in accordance with standard methods. For enzymatic hydrolysation of the conjugates of curcumin, the resultant mixture was vortex mixed for 30 seconds and incubated at 37° C. for 1 h. During incubation, samples were constantly mixed. Following incubation, 1 mL of an extraction solution (95% ethyl acetate, 5% methanol) was added before samples were vortex mixed and sonicated for 15 minutes. The resulting solution was centrifuged at 13,000 g for 10 minutes and the upper organic layer extracted to glass test tube and dried under nitrogen at 37 degrees. Samples were reconstituted with 100 µl of methanol and transferred to a HPLC limited volume insert (200 µL capacity) for chromatographic separation.

No significant differences were reported in baseline curcumin, DMC or BDMC between either group both in the parallel and crossover trial (p<0.05). Baseline plasma concentrations for all curcuminoids were undetectable via HPCL. In the crossover trial, Cmax significantly increased in the CWD90 with LipiSperse (liquid dispersible curcuminoid composition) group as demonstrated by an 807 ng/ml increase in total plasma curcuminoids from baseline values (p<0.05). Whilst the standard curcumin treatment also delivered a significant increase in total plasma curcuminoids from baseline (p<0.05), the reported Cmax for this group was significantly less than that of CWD90 with LipiSperse (p<0.05). Similar findings were seen in the parallel phase of the trial. Both treatment groups delivered significant increases in total plasma curcuminoids from baseline values (p<0.05), however Cmax values for the CWD90 with LipiSperse group were significantly greater than the standard curcumin group (p<0.05).

Temporal data for of all curcuminoids measured during the crossover and parallel phase of the trial showed that for both formulations across each phase of the trial, total plasma curcuminoid concentrations peaked at one hour following ingestion.

TABLE 1

| | GROUP 1 CWD90 Lipisperse n = 5 | | | | GROUP 2 Standard Curcumin n = 5 | | | |
|---|---|---|---|---|---|---|---|---|
| | Curcumin | DMC | BDMC | Total | Curcumin | DMC | BDMC | Total |
| $C_{MAX}$ | 691 ± 124 | 9 ± 273 | 24 ± 11 | 807 ± 155 | 215 ± 224 | 22 ± 15 | 8 ± 5 | 318 ± 154 |
| $T_{MAX}$ | 1 | 1 | 1 | 1 | 1 | 2 | 2 | 1 |
| Total $AUC_{(0-6\,H)}$ | 1549 ± 206 | 260 ± 51 | 89 ± 13 | 1898 ± 270 | 787 ± 219 | 110 ± 31 | 36 ± 10 | 933 ± 260 |
| Relative $AUC_{(0-6\,H)}$ | 258 ± 34 | 438 ± 8 | 15 ± 2 | 316 ± 45 | 131 ± 36 | 18 ± 5 | 6 ± 2 | 155 ± 43 |
| Total $AUC_{(0-24\,H)}$ | 1998 ± 288 | 366 ± 77 | 128 ± 27 | 2492 ± 392 | 1621 ± 113 | 226 ± 87 | 60 ± 21 | 1907 ± 221 |
| Relative $AUC_{(0-24\,H)}$ | 83 ± 412 | 15 ± 3 | 5 ± 1 | 104 ± 16 | 68 ± 5 | 9 ± 4 | 3 ± 1 | 79 ± 9 |

Cross-over pharmacokinetic parameters for curcumin.
DMC, BDMC, and total curcuminoids after a single 750 mg does of the two different curcumin preparations.
Values for $C_{max}$ are reported in ng/mL.
$T_{max}$ is reported in hours.
Total $AUC_{(0-6\,H)}$ is reported as ng/mL.
Relative $AUC_{(0-6\,H)}$ is reported as ng/mL/hour.
Values reported as mean ± SD.

Example 3: Enhance Bioavailability of Liquid Dispersible Curcuminoid Composition with Iron Iron is a critical micronutrient vital for oxygen transport and energy production via cellular respiration, as well as for the development and maintenance of normal neuronal function. Assuming a mixed human diet, dietary iron intake ranges from 12 to 18 mg/day, of which 1-2 mg is absorbed into the circulation via the duodenum and proximal jejunum. Due to inadequate nutrient intake, poor bioavailability on account of the complexities of iron absorption (such as the influence of dietary iron inhibitors and enhancers), gastric acidity and the effect of inflammatory status, iron intake often does not meet the body's requirements leading to widespread iron deficiency globally Iron deficiency can lead to impaired cognitive and physical development in children, compromise physical and cognitive performance in adults, and has been linked with fatigue, impaired quality of life, and reduced mood.

Hippocampal brain-derived neurotrophic factor (BDNF) is a neurotrophic growth factor which is suggested to be essential for normal neuronal development and cognitive function. As well as being essential for maintaining the normal function of mature neurons, BDNF is also implicated in dendrite growth, spinal development, learning and memory formation, energy homeostasis. Therefore, it is thought that increased levels of BDNF could enhance cognitive capacity and potentially lead to reduced fatigue Although, the mechanistic pathways of iron and BDNF interaction are not yet fully elucidated, optimal iron levels are thought to be essential for BDNF homeostasis.

Curcumin is a pleiotropic compound with wide ranging beneficial properties including antioxidative, anti-inflammatory and neuroprotective effects, with potential as a treatment for neurological disorders, such as depression, bipolar disorders and neurodegenerative diseases. However, this potential may be limited by curcumin's access to the brain at therapeutic concentrations as it is rapidly metabolised following ingestion. The pharmacological use of curcumin has therefore been limited due to its poor bioavailability, limited bio-distribution, poor stability and short half-life.

As iron and curcumin independently have both been associated with BDNF homeostasis in animal and cellular models, a 6-week, double blind, randomized, placebo-controlled study was performed to examine the effects of oral iron supplementation at low (18 mg) versus high (65 mg) ferrous iron dosages, either alone or co-administered with curcumin (500 mg) supplementation on serum BDNF levels in healthy adults. The study was designed to determine whether co-administration of ferrous sulphate and formulated curcumin supplement (a liquid dispersible curcuminoid composition according to the present invention; commercially available HydroCurc™ produced by Gencor Pacific Ltd., Lantau Island, Hong Kong) would amplify serum levels of BDNF.

Materials and Methods 3.1 Study Design

The present double blind, placebo-controlled, randomized study recruited 155 healthy participants (79 males and 76 females) for a study duration of 6 weeks. Sample size was calculated using G*Power statistical analysis software to achieve 80% power.

Study participants were randomly allocated to one of five different treatment groups using the online service by Study Randomizer (2020), via a permuted block and gender balanced randomisation algorithm with 31 participants in each group. The 5 different treatment groups were ferrous sulphate and curcumin placebos (FS0+Plac), ferrous sulphate (18 mg elemental iron) and curcumin placebo (FS18+Plac), ferrous sulphate (18 mg elemental iron) and 500 mg curcumin (FS18+Curc), ferrous sulphate (65 mg elemental iron) and curcumin placebo (FS65+Plac) and ferrous sulphate (65 mg elemental iron) and 500 mg curcumin (FS65+Curc) (FIG. 1). Healthy adults aged between 18 to 40 years, whose ferritin levels were in the normal physiological range were recruited into the study.

Normal ferritin was defined as 15-300 µg/L for men and 15-200 µg/L for women, according to United Kingdom (UK) guidelines. Any participants with haemoglobin values below the WHO cut-off for anaemia (WHO, 2017) were not enrolled in the study (<130 g/L for men and <120 g/L for women). Any participants with haemoglobin values below the WHO (2017) cut-off for anaemia were not enrolled in the study. For the purpose of the sub-analysis, participants were grouped according to baseline ferritin values, <50 µg/L was categorised as 'low' and ≥50 µg/L as 'normal' ferritin values.

Exclusion criteria included the following: any diagnosis of medical conditions or comorbidities, currently trying to conceive, pregnancy or lactating and/or any chronic menstrual disorders or menopausal changes.

3.2. Supplementation

As per FIG. 1, participants were provided two different doses (high and low dose) of ferrous sulphate supplements, co-administered with a dose of curcumin or equivalent placebo(s) (depending on supplement group allocation). The high dose ferrous sulphate supplement (200 mg/day, with 65 mg elemental iron) is the first line oral iron therapy for treatment and prophylaxis of iron deficiency and iron deficiency anaemia worldwide. The low dose ferrous sulphate (55 mg/day with 18 mg elemental iron) is 100% of the Daily Value (DV) of iron in the United States (Food and Drug Administration Center for Food Safety and Applied Nutrition, 2013). Curcumin supplements were in the form of 500 mg/day of a liquid dispersible curcuminoid composition (HydroCurc™). This formulation contains 85% total curcuminoids (wherein the curcuminoids comprise 80% curcumin, 17% DMC and 3% BDMC) entrapped in a proprietary micellar delivery system that was shown to have enhanced bioavailability and a deliver a higher therapeutic dose, known as lipisperse (i.e., the dispersing agent of the present invention). The 500 mg dose of the curcumin supplements comprises approximately 10% (w/w) lipsperse (dispersing agent) and were produced according to the methods described herein for the liquid dispersible curcuminoid composition. Microcrystalline cellulose served as a placebo as well as the bulking agent in the capsules of active ingredients. White-opaque hydroxypropyl methylcellulose (HPMC) capsules were used, size of #1 and #00, for the ferrous sulphate and curcumin supplements, respectively. The supplements were presented in white, screw lid bottles, labelled with the related group codes. The participants were required to take one ferrous sulphate and one curcumin supplement per day with water, at least 2 hours after or 1 hour before food consumption at separate times.

3.3. Blood Collection

Participants attended blood collection appointments following an overnight fast (12 hour fast). Venous blood samples were collected at baseline, mid-point (21 day) and end-point (42 day) visits from the antecubital fossa by venepuncture (using a 21 g needle). Approximately 10 ml of blood was collected from each participant per procedure using Becton Dickinson (BD) Vacutainer® serum-separating tubes (SST) (BD, Oxford, UK). Blood in the SST were left to coagulate at room temperature for 45 minutes and then centrifuged (Hettich 340r, Hettich GmbH & Co. KG, Tuttlingen, Germany) for 10 minutes at 3857 g. Serum supernatant was aliquoted into 1.5 ml microcentrifuge tubes post centrifugation and stored at −80° C.

3.4. Ferritin Assay

Serum ferritin samples were analysed using a Horiba ABX Pentra 400 (Horiba Ltd, Kyoto, Japan) multiparametric medical bench top chemistry analyser, compliant with the National Committee for Clinical Laboratory Standards (NCCLS) (Coudène et al., 2005). With Horiba ABX Ferritin 2 CP reagents, ferritin values were determined by latex-enhanced immunoturbidimetric assay, in accordance with the manufacturers protocol and as previously described by Polacchini et al (2015).

3.5. BDNF Assay

Serum was assayed for BDNF levels using the Biosensis Mature BDNF Rapid™ enzyme-linked immunosorbent assay (ELISA) Kit (ATI Atlas, Chichester, UK) following manufacturer's protocol using dilution factor of 1:100. Pre-coated microplates were incubated with 100 μL of diluted BDNF standards, quality control (QC) samples, serum samples (1:100) or blanks (sample diluent only) for 45 minutes on a plate shaker (140 rpm), at room temperature (RT). Plates were then washed five times with wash buffer (200 μL per well). After the addition of 100 μL detection antibody per well, the plates were incubated on the plate shaker (140 rpm at RT) for 30 minutes. Following five more washes, 100 μL of 1× streptavidin-HRP conjugate was added to each well. The plates were incubated for a further 30 minutes at 140 rpm (RT). The plates were then washed 5 times and 100 μL of 3,3',5,5'-Tetramethylbenzidine (TMB) was added to each well and incubated at RT for 9 minutes in the dark before the addition of 100 μL of stop solution into each well. The absorbance was read with a microplate reader (SPECTROstar Nano, BMG Labtech) at 450 nm (within 5 minutes).

3.6. Statistical Analysis

Values are expressed as mean±Standard Error of Mean (SEM). The BDNF assay results were statistically analysed using a two-way, repeated measures analysis of variance (ANOVA) or mixed effects model (where missing values were present). Post-hoc tests (Sidak's and Tukey's) were carried out to assess differences between and within treatment groups (PRISM software package, Version 8, Graphpad Software Inc., San Diego, USA).

3.7. Results

Of the 155 participants recruited, 150 completed all study visits. Two participants withdrew from the FS0+Plac groups, one from nausea after the baseline visit and one from loss of interest in the study after the midpoint visit. One participant also withdrew from the FS65+Curc group after the baseline visit due to loss of interest and another withdrew due to gastric distress. A participant in the FS18+Plac group was excluded from the study due to incomplete blood sampling at the mid-point.

The mean age of participants was 26.12 years (±0.39). There was no significant difference in mean age between the 5 treatment groups. There were also no significant differences observed in anthropometric measurements of participants (table 1). The study population was of mixed ethnicity, representative of the central London population where the recruitment took place.

TABLE 1

Participant age, weight, height, body mass index (BMI) and body fat percentages (mean ± SEM).

| Variable | FS0 + Plac | FS18 + Plac | FS18 + Curc | FS65 + Plac | FS65 + Curc |
|---|---|---|---|---|---|
| Age (yrs) | 26.29 ± 0.84 | 25.84 ± 0.93 | 24.48 ± 0.82 | 27.23 ± 0.83 | 26.77 ± 0.87 |
| Weight (kg) | 70.79 ± 2.37 | 72.45 ± 3.13 | 66.17 ± 2.45 | 70.21 ± 3.54 | 67.70 ± 2.13 |
| Height (m) | 1.72 ± 0.02 | 1.71 ± 0.01 | 1.68 ± 0.02 | 1.70 ± 0.02 | 1.72 ± 0.02 |
| BMI (m/kg$^2$) | 23.89 ± 0.58 | 24.51 ± 0.85 | 23.32 ± 0.64 | 24.11 ± 1.00 | 22.83 ± 0.55 |
| Body fat (%) | 25.27 ± 1.71 | 24.96 ± 1.67 | 24.32 ± 1.76 | 24.97 ± 1.54 | 23.39 ± 1.39 |

At baseline, no significant differences were observed in mean ferritin levels across the treatment groups (table 2). However, there was a significant difference observed in baseline BDNF levels between the FS18+Plac (37.28 pg/ml) and FS18+Curc (30.28 pg/ml) groups, with the mean BDNF being 22.7% higher in the FS18+Plac group compared to the FS18+Curc group (table 3). No significant differences in baseline BDNF were observed when comparing any of the other groups (table 2).

TABLE 2

Participant baseline ferritin and BDNF levels expressed as mean ± SEM.

| Variable | FS0 + Plac | FS18 + Plac | FS18 + Curc | FS65 + Plac | FS65 + Curc |
| --- | --- | --- | --- | --- | --- |
| Ferritin (μg/L) | 58.71 ± 9.37 | 68.58 ± 10.30 | 52.36 ± 7.74 | 55.14 ± 8.18 | 61.46 ± 8.47 |
| BDNF (pg/ml) | 35.18 ± 2.10 | 37.16 ± 1.88 | 30.28 ± 1.54 | 31.59 ± 1.35 | 30.85 ± 8.47 |

When evaluating the effect of treatment group on serum BDNF levels after 21 day (midpoint) and 42 day (endpoint) supplementation, significant differences were observed between the different treatment groups (F (4, 144)=2.746, p=0.031) and the two time points (F (1, 142)=11.36, p=0.001). A significant increase of 26.34% in BDNF levels from midpoint to endpoint was observed in participants taking FS18+Curc (p=0.024) (FIG. 2). At the end point, there was also a significant difference observed in BDNF levels between the FS18+Curc and FS18+Plac groups (p=0.042), with the FS18+Curc treatment resulting in a 34.94% higher concentration of BDNF than FS18+Plac (FIG. 2). A similar trend of increased BDNF was observed at the endpoint when comparing the FS65+Curc treatment with FS65+Plac, however this was not significant (FIG. 2).

4 & 5). In the low ferritin sub-group (table 4), significant differences were observed between baseline, mid-point and end-point time points (F (2, 158)=27.81, p<0.0001). A significant increase of 35.17% in ferritin levels was observed at endpoint compared to baseline in the FS18+Curc group (p=0.0013) (table 4). A significant increase of 58.75% in ferritin levels was also observed at endpoint compared to baseline in the FS65+Curc group (p=0.0002) (Table 4). Furthermore, there were significant increases from baseline for the FS65+Plac group at mid-point (43.6%) and end-point (68.34%) (p=0.0014 and p<0.0001, respectively) (table 4). In the normal ferritin sub-group, there was no significant effect observed in ferritin values over time or between groups in relation to any supplementation (table 5).

TABLE 4

Mean Ferritin (μg/L) values (low ferritin sub-group) per treatment group/timepoint (mean ± SEM).

| Timepoint | FS0 + Plac | FS18 + Plac | FS18 + Curc | FS65 + Plac | FS65 + Curc |
| --- | --- | --- | --- | --- | --- |
| Baseline | 25.08 ± 1.73 | 25.29 ± 2.81 | 30.25 ± 2.52 | 25.55 ± 1.78 | 25.04 ± 2.72 |
| Mid-point | 28.23 ± 2.96 | 34.59 ± 4.24 | 36.45 ± 2.92 | 36.69 ± 3.34 ** | 32.10 ± 4.04 |
| End-point | 31.39 ± 5.12 | 33.31 ± 3.39 | 40.89 ± 4.99 ** | 43.01 ± 4.01 **** | 39.75 ± 6.19 *** |

*represents significance values when comparing midpoint or endpoint to baseline within the same condition
** p < 0.01,
*** p < 0.001,
**** p < 0.0001

TABLE 5

Mean Ferritin (μg/L) values (normal ferritin sub-group) per treatment group/timepoint (mean ± SEM).

| Timepoint | FS0 + Plac | FS18 + Plac | FS18 + Curc | FS65 + Plac | FS65 + Curc |
| --- | --- | --- | --- | --- | --- |
| Baseline | 91.38 ± 12.94 | 109.17 ± 13.30 | 98.79 ± 15.37 | 94.54 ± 9.94 | 100.31 ± 10.01 |
| Mid-point | 93.37 ± 13.75 | 100.10 ± 16.85 | 102.23 ± 13.56 | 101.50 ± 11.75 | 101.63 ± 11.45 |
| End-point | 87.88 ± 11.45 | 100.21 ± 13.27 | 102.32 ± 16.18 | 98.37 ± 15.49 | 106.62 ± 12.29 |

There were no other significant differences in BDNF levels between or within treatment groups (FIG. 2).

When participants were sub-grouped according to low ferritin (<50 μg/L) and normal ferritin (≥50 μg/L) values, a significant increase in BDNF from midpoint to endpoint was observed in the cohort with low ferritin who were supplemented with FS18+Curc (p=0.019) (FIG. 3A). Although no significant difference in BDNF was observed between the FS18+Curc and FS18+Plac group for participants with low baseline ferritin, the FS18+Curc group had significantly higher BDNF at the endpoint compared to the FS0+Plac group, (increased by 53.78%, p=0.028) (FIG. 3A). No significant differences in BDNF levels were observed between treatment groups, at either time point, in participants with normal ferritin levels (FIG. 3B).

No significant differences were observed in baseline ferritin levels between the low and normal ferritin groups (table These findings indicate that increased BDNF levels could help to improve cognitive function.

Data from the current study were sub-grouped into 'low' (<50 μg/L) ferritin and 'normal' (≥50 g/L) ferritin participants (FIGS. 3A and 3B, respectively). Participants with serum ferritin below 50 μg/L, showed the same trend (increased levels) as the overall data for serum BDNF, with the FS18+Curc treatment leading to increased BDNF from midpoint to endpoint (FIG. 3A). However, no significant differences were recorded for participants with normal ferritin levels. This suggests that the addition of curcumin to 18 mg iron supplementation, in particular, may be most effective at enhancing serum BDNF levels in individuals with low ferritin levels. Notably, in participants who had 'low' ferritin at baseline, all groups containing iron supplementation showed significant increases in ferritin values apart from the FS18+Plac group. This indicates that the addition of curcumin alongside low dose iron supplementation may contribute to enhanced ferritin formation, which may indicate enhanced intestinal iron uptake over time. Together these results suggest that curcumin may enhance the effects of low dose iron supplementation, in particular for those individuals with iron deficiency.

Compared to conventional curcumin, the liquid dispersible curcuminoid compositions of the present invention used in this study (HydroCurc) resulted in significantly greater increases in total plasma curcuminoid concentration. This could therefore explain how the addition of curcumin to iron supplementation consistently resulted in increased BDNF levels in the current study.

In summary, the current study demonstrates for the first time that co-administration of formulated curcumin with ferrous sulphate containing 18 mg elemental iron for 42 days results in increased serum BDNF levels. The addition of curcumin may therefore provide a novel approach to iron supplementation and possibly enhance the iron associated cognitive benefits linked to increased serum BDNF levels.

I claim:

1. A method of increasing serum levels of BDNF in a subject, comprising administering to the subject a liquid dispersible curcuminoid composition comprising curcuminoid and a dispersing agent, wherein the liquid dispersible curcuminoid composition is administered in combination with a source of iron, wherein the source of iron is a compound, composition or supplement that comprises at least 18 mg elemental iron, wherein the liquid dispersible curcuminoid composition is prepared by combining the curcuminoid with the dispersing agent whilst applying a shear force, and wherein administration to the subject of the liquid dispersible curcuminoid composition with the source of iron acts synergistically to increase BDNF serum levels compared to administration of the same or equivalent doses of the liquid dispersible curcuminoid composition and the source of iron when administered alone.

2. The method of claim 1, wherein the dispersing agent comprises a carrier oil, a non-ionic surfactant and a solvent, and wherein the ratio of the curcuminoid and the dispersing agent is from about 10:1 to about 5:1.

3. The method of claim 1, wherein the liquid dispersible curcuminoid composition comprises at least 70% (w/w), at least 80% (w/w), at least 85% (w/w), at least 90% (w/w), or at least 95% (w/w) total curcuminoids.

4. The method of claim 1, wherein the liquid dispersible curcuminoid composition comprises curcumin.

5. The method of claim 2, wherein the dispersing agent comprises 30% (w/w)-90% (w/w) non-ionic surfactant.

6. The method of claim 2, wherein the dispersing agent comprises 5% (w/w)-30% (w/w) carrier oil.

7. The method of claim 2, wherein the dispersing agent comprises 1% (w/w)-10% (w/w) solvent.

8. The method of claim 1, wherein the source of iron is a compound, composition or supplement that comprises at least 50% (w/w), at least 60% (w/w), at least 70% (w/w), at least 80% (w/w) or at least 90% (w/w) ferrous sulfate, ferrous gluconate, ferrous fumarate, or combinations thereof.

9. The method of claim 1, wherein the source of iron is a compound, composition or supplement that comprises at least 100% (w/w), at least 15% (w/w), at least 20% (w/w), at least 25% (w/w) or at least 30% (w/w) elemental iron.

10. The method of claim 1, wherein the ratio of the liquid dispersible curcuminoid composition and the source of iron is from about 10:1 to about 2:1.

11. The method of claim 1, wherein the ratio of total curcuminoids and elemental iron is from about 30:1 to about 5:1.

* * * * *